(12) United States Patent
Henn

(10) Patent No.: US 8,415,344 B2
(45) Date of Patent: Apr. 9, 2013

(54) METHOD OF TREATING DEPRESSION

(75) Inventor: Fritz Henn, East Patchogue, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 13/307,033

(22) Filed: Nov. 30, 2011

(65) Prior Publication Data

US 2012/0129826 A1     May 24, 2012

Related U.S. Application Data

(62) Division of application No. 12/641,968, filed on Dec. 18, 2009, now Pat. No. 8,101,600.

(51) Int. Cl.
*A61K 31/13*     (2006.01)
*A61K 31/44*     (2006.01)
*A61K 31/541*     (2006.01)

(52) U.S. Cl. ............... 514/223.2; 514/353; 514/663

(58) Field of Classification Search ............... 514/198, 514/192, 200
See application file for complete search history.

(56) References Cited

U.S. PATENT DOCUMENTS

| 6,610,324 B2 * | 8/2003 | Stoll .................... 424/464 |
| 6,627,625 B1 * | 9/2003 | Koppel ................. 514/198 |
| 6,667,317 B2 * | 12/2003 | Chenard et al. ........ 514/323 |
| 7,605,185 B2 * | 10/2009 | Graupner .............. 514/725 |

* cited by examiner

*Primary Examiner* — Jennifer M Kim
(74) *Attorney, Agent, or Firm* — Dorene M. Price

(57) ABSTRACT

Methods for treatment of depression-related mood disorders in mammals, particularly humans are disclosed. The methods of the invention include administration of compounds capable of enhancing glutamate transporter activity in the brain of mammals suffering from depression. ATP-sensitive $K^+$ channel openers and β-lactam antibiotics are used to enhance glutamate transport and to treat depression-related mood disorders and depressive symptoms.

2 Claims, 2 Drawing Sheets

Astrocytic Glutamate Transporter mRNA levels

METHOD OF TREATING DEPRESSION

This application is a divisional application of U.S. patent application Ser. No. 12/641,968 filed Dec. 18, 2009, itself a non-provisional application claiming the benefit of U.S. Provisional Patent Application Ser. No. 61/140,150 filed Dec. 23, 2008, each of which applications is hereby incorporated by reference in its entirety.

GOVERNMENT SUPPORT

This invention was made with Government support under contract number DE-AC02-98CH10886, awarded by the U.S. Department of Energy. The Government has certain rights in the invention.

BACKGROUND OF THE INVENTION

1. Field of the Invention

The present invention relates to a method of treating depression or depression-related disorders. More specifically, the invention relates to a method of treating depression and depression-related disorders by administration of compounds that increase astrocyte glutamate transport, such as $K_{ATP}$ channel openers and/or compounds capable of stimulating glutamate transporter expression.

2. Background of the Invention

It is the rare individual who has not been beset, at least once in his or her life, with a bout of sadness or "the blues" leading to an inability to perform daily tasks with the usual vigor and little enjoyment in life. In most cases, these occurrences are brought on by recognizable events, such as a divorce, loss of a loved one, or work-related stress. In most cases, these occurrences pass after a reasonable period of time and the individual returns to a normal routine. However, for many such individuals, that normal routine never returns, but rather the individual's routine becomes depression. In extreme cases, the condition becomes so severe that the individual becomes completely unable to cope with the relatively minor stresses of everyday life. Often such individuals are overwhelmed by feelings of fatigue, hopelessness, worthlessness, guilt, and thoughts of suicide.

Although to date no single cause of clinical depression has been identified, it is now generally accepted that there is likely a neurochemical component to it. Typical treatments now often consist of a combination of psychotherapy and medication. Currently, the most commonly used antidepressant medications function generally to regulate brain neurotransmitters such as dopamine, serotonin and norepinephrine. Two classes of compounds, one known as selective serotonin reuptake inhibitors, or SSRIs, and the other known as serotonin and norepinephrine reuptake inhibitors (SNRIs) are widely prescribed for treatment of depression. These antidepressants, such as fluoxetine (Prozac®), sertraline (Zoloft®), venlafaxine (Effexor®) and duloxetine (Cymbalta®) have gained substantial popularity because they cause fewer side effects than earlier antidepressants, such as monoamine oxidase inhibitors (MAOIs). Notwithstanding their improved tolerability, however, SSRIs and SNRIs still cause their share of side effects, including insomnia, nausea and sexual dysfunction. In addition to the associated problems, a major concern with known antidepressants is the time they take to achieve their desired effect. In most cases, it will be a minimum of three to four weeks before a full relief of symptoms is observed. In the case of severe depression, this delay can sometimes be life-threatening. Furthermore, only about two-thirds of patients treated actually respond to modern antidepressants. Thus, there continues to be a need for development of new antidepressant medications that will avoid some or all of the problems observed with those antidepressants currently in use. Based on a novel observation regarding the neurochemical basis for depression, the present invention fills such a need.

SUMMARY OF THE INVENTION

The present invention relates to methods of treating depression-related mood disorder in a mammal in need of such treatment comprising administering to the mammal an effective amount of a compound that increases astrocyte glutamate transport including an effective amount of an ATP-sensitive potassium ($K_{ATP}$) channel opener or an effective amount of a compound capable of enhancing expression of the glutamate transporter gene GLT1. In preferred embodiments, the mammal is a human.

Compositions useful for treating depression-related mood disorder and depressive symptoms comprising $K_{ATP}$ channel openers are an aspect of the invention. Compositions comprising $K_{ATP}$ channel openers are selected from the group consisting of diazoxide, pinacidil and iptakalim.

Compositions that elevate the expression of the glutamate transporter gene GLT1 are another aspect of the invention as they are useful for treating depression-related mood disorder and depressive symptoms.

Compositions useful for treating depression-related mood disorder comprising effective amounts of a β-lactam antibiotic are a further aspect of the invention.

DETAILED DESCRIPTION OF THE INVENTION

The present invention is based on observations relating to the role of the lateral habenula in depression. The habenula is an area of the epithalamus of the brain that is known to be involved in the control of emotional and social behaviors, circadian rhythms and cognitive functions. In particular, the lateral habenula has been associated with negative emotional behaviors, such as schizophrenia, drug-induced psychosis and depression (Sandyk R (1992) Int. J. Neurosci. 67:19-30. Scheibel A B (1997) Neuropsychiatry Clin. Neurosci. 9:342-353). Studies attempting to elucidate the neurological basis of learned helplessness (LH), a widely accepted animal model of depression (Vollmayr, B. and Henn, F. A., (2003), Clin. Neurosci. Res. 3: 245-251), have shown histochemical differences in the habenula of LH rats (J. Shumake and F. Gonzalez-Lima, Behav. Cogn. Neurosci. Rev. 2: 198-221 (2003).

Our recent unpublished studies demonstrated that the habenula of helpless rats exhibited ten times the cell firing rate compared with non-helpless rats. It has been suggested that depression is associated with increased activation of the lateral habenular nucleus, resulting in the down-regulation of the serotonergic, noradrenergic and dopaminergic systems, and stimulation of the hypothalamic-pituitary-adrenal axis (A. Sartorius and F. Henn, Medical Hypotheses (2007) 69: 1305-1308). To date, however, the physiological mechanism by which the lateral habenula becomes overactivated, and/or participates in the development of negative emotional conditions, particularly depression, has remained unclear.

The glutamatergic neurotransmitter system of the brain is known to be involved in memory function and information processing, and glutamate is the most common neuroexcitatory transmitter in the mammalian central nervous system. After release in neurotransmission, glutamate transporters, located in neuronal and glial membranes, ensure that glutamate is removed from the extracellular spaces, ending the transmission, and recycling the glutamate for future use. Accumulation of excess glutamate can ultimately cause neuronal cell death due to excitotoxicity.

Figure 1:
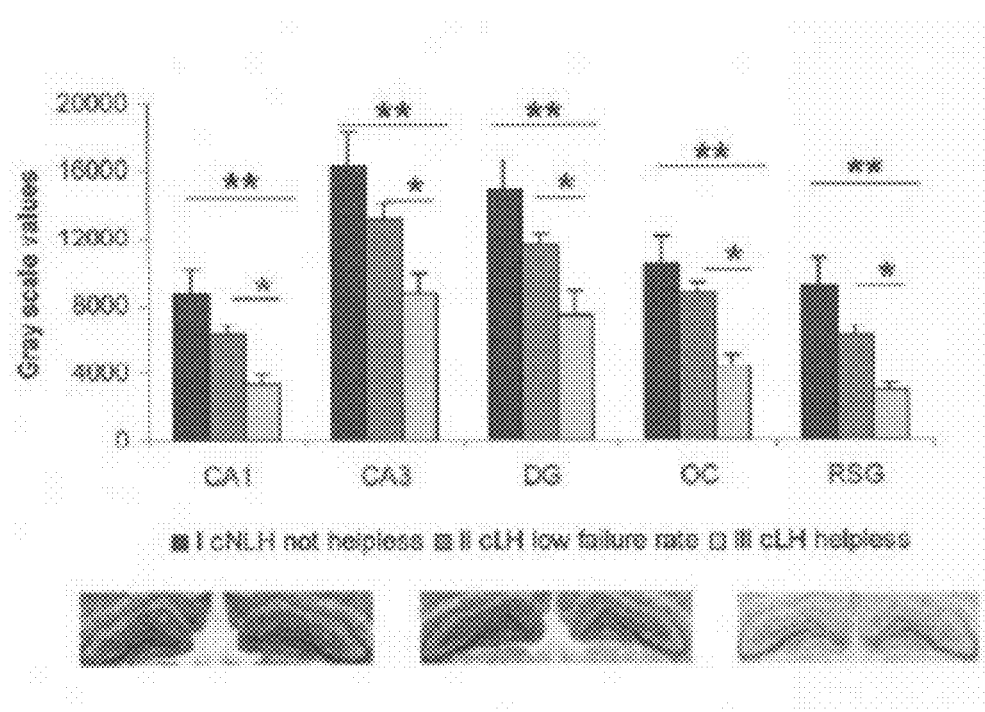
FIG. 1 illustrates the results of in situ hybridization experiments to determine the level of expression of mRNA encoding the glutamate transporter GLT1 in habenular astrocytes of learned helpless (LH) and not helpless (nLH) rats. CA: cornus ammonis; DG: dentate gyrus; OC: occipital cortex; RSG: retrosplenial cingulated cortex.

In studies on the whole brain performed in connection with this invention, it was unexpectedly discovered that mRNA encoding GLT1, a glutamate transporter, is significantly decreased in astrocytes of LH rats (FIG. 1). Subsequently, it was further demonstrated that glutamate uptake in the LH rats is suppressed relative to non-LH rats. This observation is, to the inventor's knowledge, the first time that suppression of glutamate transport has been shown to be associated with depression. The accumulation of glutamate due to the inadequate glutamate transport would be one explanation for the observed overactivity of the habenula in LH rats and humans exhibiting depression, and thereby provides two heretofore unrecognized potential targets for antidepressant drugs, i.e., ATP-sensitive potassium ($K_{ATP}$) channels and glutamate transporter, GLT1, expression control elements.

Expression of the GLT1 gene in astrocytes has been shown to be enhanced by administration of various β-lactam antibiotics (Rothstein, et al., Nature (2005) 433:73-77 and Lipski, et al. Neuroscience (2007) 146:617-629). Ceftriaxone, a representative cephalosporin, was found to be a particularly effective antibiotic in studies of neuroprotection. Embodiments of the present invention contemplate that depression-related mood disorder may be treated by enhancement of habenular astrocyte glutamate transporter expression through the administration of β-lactam antibiotics, including but not limited to cephalosporins such as ceftriaxone and penicillin and derivatives of penicillin.

ATP-sensitive potassium ($K_{ATP}$) channels are widely distributed in various mammalian tissues, such as cardiac muscle, smooth muscle, skeletal muscle, the pancreas and neurons. $K_{ATP}$ channels play important roles in a variety of tissues by coupling cellular metabolism to electrical activity. The $K_{ATP}$ channel is an octameric complex of two unrelated proteins: a pore-forming subunit, Kir6.x, which forms an inwardly rectifying K+ channel and an ATP binding cassette transporter, also known as the sulfonylurea receptor (SURx) (Babenko, et al., Annu. Rev. Physiol., (1998) 60:667-687). Each of these proteins can exist in different isoforms or subspecies, the various combinations of isoforms are apparently characteristic of certain tissues. For example, the combinations of Kir6.2 with either SUR1 or SUR2B are characteristic of neuron $K_{ATP}$ channels, while astrocyte $K_{ATP}$ channels are composed of Kir6.1 and SUR1 (A. Thomzig et al., Mol. Cell. Neurosci. (2001) 18: 671-690).

One critical aspect of the function is the coupling of cellular metabolism to electrical activity. More specifically, depending on the tissue in which they are found, they can regulate or modulate a variety of physiological activities, including insulin secretion, action potential frequency and release of neurotransmitters. The latter function is particularly important in brain tissue, where they are present in both pre- and post-synaptic membranes as well as glial cells. When functioning normally, these channels ultimately ensure the proper distribution of neurotransmitters, thereby regulating cell excitability. Under natural conditions, the channels are regulated by the ratio of ATP to ADP in the cell, with ATP causing channel closing, and ADP inducing channel opening. However, because of their widespread and critical physiological functions, they have become a target of drug development, giving rise to a chemically diverse group of compounds generically referred to as $K_{ATP}$ channel openers (also referred to as KCO's), which act as agonists of $K_{ATP}$ channel activity.

$K_{ATP}$ channel openers have found a variety of putative and actual pharmacological uses, including treatment of hypertension, angina, congestive heart disease, COPD, asthma, incontinence, myotonic dystrophy, alopecia and glaucoma. Their role in regulating neurotransmission has also led to suggestions that they may be useful in treatment of Parkinson's disease, epilepsy, analgesia, and prevention of neurodegeneration (X-L. Sun et al., Neuropsychopharmacology (2003) 33: 1336-1342 (2003), by virtue of observation that they are capable of stimulating transport of excess glutamate from extracellular spaces in astrocyte culture. However, there has been no previous recognition of a role of $K_{ATP}$ channels in the genesis of mood disorders, particularly depression, and the $K_{ATP}$ channel openers have not previously been suggested as possible therapeutic agents for such conditions.

It has now been surprisingly demonstrated that $K_{ATP}$ channel openers provide a unique approach to the treatment of depression in mammals. As shown in Example III below, administration of a $K_{ATP}$ channel opener to a mammal exhibiting learned helplessness, an animal model for human depression, relieves the associated symptoms that characterize depression. Thus, the present inventions provide a new method of treatment of depression, the method comprising administering to an individual in need of such treatment an effective amount of at least one $K_{ATP}$ channel opener. One advantage of the present method includes its ability to produce remission of depressive symptoms in as little as 2-3 days, a tremendous improvement over existing methodologies that can take several weeks to be effective. In addition, many $K_{ATP}$ channel openers are already known for use in other types of therapy (for example, hypertension), and have an established record of safe use in humans.

The active agent in the method of the invention may be any $K_{ATP}$ channel openers that are capable of stimulating uptake of glutamate by astrocytes. $K_{ATP}$ channel openers are known to exist in the following classes of compounds: benzopyrans, cyanoguanidines, thioformamides, benzo- and pyridothiadizines, pyridyl nitrates, pyrimidine sulfates, cyclobutenediones, dihydropyridine-related structures, and tertiary carbinols (R. Mannhold, Med. Res. Rev. (2004) 24 (2): 213-266; WO2006/026469; the contents of each of these is incorporated herein by reference). Examples of benzopyran compounds include, but are not limited to, cromakalim, levcromakalim, emakalim, bimakalim, celikalim, U96501, RO 31-6930, SDZ PCO 400, KC-399, KC-515, BRL 49381, JTV-506, NIP-121, and rilmakalim. (J. M. Evans and G. Stemp, in Potassium Channels and their Modulators (1997), Evans et al., Eds, Taylor & Lord, London, pp. 27-55). Exemplary cyanoguanidine compounds are pinacidil and AL0670 (P. W. Manley and U. Quast, (1992) J. Med. Chem. 35: 2327-2340). Thioformamide channel openers include aprikalim, picartamide, RP49356, and MCC-134 (T. J. Brown et al., J. Med. Chem. (1992) 35: 3613-3624; M. N. Palfreyman et al. in Potassium Channels and their Modulators (1997), Evans et al., Eds, Taylor & Lord, London, pp. 57-77). Benzo- and pyridothiadiazine compounds include diazoxide, BPDZ-44, BPDZ-79, and BPDZ-83 (B. Pirotte et al. J. Med. Chem. (1993) 33: 3211-3213; P. DeTullio, et al., J. Med. Chem. (1996): 39: 937-948; S. Khelili et al., Bioorg. Med. Chem. (1999) 7: 1513-1520; B. Pirotte et al., J. Med Chem. (2000) 43: 1456-1466). Pyridyl nitrates include nicorandil, FK336, KRN 2391, and Ki1769. Exemplary of pyrimidine sulfates is minoxidil. Exemplary cyclobutenediones are the compounds WAY-1333537 and WAY-151616 (J. A. Butera et al., J. Med. Chem. (2000) 43: 1187-1202; A. M. Gilbert et al., J. Med Chem (2000) 43: 1203-1214; J. A. Butera and T. M. Argentieri, Drugs Fut. (2000) 25: 239-245. Dihydropyridine-related structures include the compounds ZM-244805, ZD-0947, and A-278637 (S. Trivedi et al., Res. Commun. Mol. Pahtol. Pharmacol. (1995) 88: 137-151; W. D. Steers, Curr. Opin. Center. Peripher. Nerv. Syst. Invest. Drugs (2000) 2: 220-231; M. Gopalakrishnan et al. J. Pharmacol. Expl Ther. (2002) 303: 379-386; I. Drizin et al., Bioorg. Med. Chem. Lett. (2002) 12. 1481-1484. In addition, iptakalim is a lipophilic, low molecular weight para-amino $K_{ATP}$ channel opener. (H. Wang, Acta Pharmalogica Sinica (1998) 19: 397-402; Drug Dev. Res. (2003) 58: 65-68; H. Wang, Drug Dev. Res. 54 (2002) 240-241).

$K_{ATP}$ channel openers useful in the present invention are specifically those that are capable of stimulating the uptake of glutamate by astrocyte glutamate transporters. Examples of $K_{ATP}$ channel openers shown to be effective for this purpose are diazoxide, pinacidil and iptakalim (Sun et al., supra). With regard to other $K_{ATP}$ channel openers, their potential suitability for use in the present method can be confirmed by their performance in the known glutamate uptake assay, a procedure described by Yao et al., ((2005) J. Neurochem. 92: 948-961), the paragraph found on page 951 headed "Uptake of D,L-[3H]glutamate" of which is incorporated herein by reference. Briefly, the process is as follows: following administration of the candidate channel opener for 48 hours, uptake assays are initiated by adding D,L-[3H]glutamate to reaction flasks covered with astrocytes, and incubated eat 37° C. Non-specific uptake is determined from samples incubated at 0° C., and the values are subtracted from the total. All reactions are terminated by rinsing three times with ice-cold 0.9% NaCl. Cells are then lysed immediately with 0.3 M NaOH. After centrifugation at 10,000 rpm for 15 minutes, supernatant is abstracted and radioactivity is determined by liquid scintillation counter. The protein content of each sample is determined using methods standard in the art.

In one embodiment, the channel opener is selected from among the benzothiadiazines, preferably diazoxide. In another embodiment, the channel opener is selected from among the cyanoguanidines, preferably pinacidil. In yet another embodiment, the channel opener is iptakalim. Specifically less preferred are channel openers from the pyridyl nitrate (such as nicorandil), and pyrimidine sulfate (such as minoxidil) classes of channel openers; compounds in these groups have proven less effective than, for example, diazoxide, at the dosages tested.

The antidepressant-effective $K_{ATP}$ channel openers of the invention can be used for treatment of a variety of depression-related mood disorders. For purposes of the present invention, the term "mood disorders" is to be understood as encompassing those conditions defined as mood disorders in the Diagnostic and Statistical Manual of Mental Disorders, Fourth Edition, 1994 ("DSM-IV"), the contents of which are incorporated herein by reference. More specifically, the mood disorders to be treated in accordance with the present invention include those associated with the occurrence of more than one depressive symptom, such as depressed mood, loss of interest or pleasure, loss of appetite, sleep disturbance, psychomotor changes, fatigue, a sense of worthlessness, impaired concentration or thoughts of death, the symptoms typically being exhibited over a prolonged period of time. In one embodiment, the channel openers are used to treat those conditions defined in DSM-IV as being associated with a Major Depressive Episode, i.e., a period of at least two weeks in which the individual to be treated exhibits either depressed mood, or the loss of interest or pleasure, associated with at least four additional depressive symptoms from the list cited above. Examples of such conditions include Major Depressive Disorder, Bipolar I Disorder, and Bipolar II Disorder. In another embodiment, the condition to be treated is characterized by depressive symptoms that do not necessarily rise to the level of a Major Depressive Episode, such as Dysthymic Disorder, Depressive Disorder Not Otherwise Specified, Cyclothymic Disorder, Bipolar Disorder Not Otherwise Specified, Mood Disorder Due to a General Medical Condition, and Substance-Induced Mood Disorder. In another embodiment, the effective channel openers can be used to treat isolated Major Depressive Episodes that are not characterized by DSM-IV as a defined disorder, for example, those associated with post-partum depression as well as depressive symptoms associated with mental conditions that are not formally classified as mood disorders, for example, Schizoaffective Disorder or Seasonal Affective Disorder. In yet another embodiment, the channel openers can be used to treat an individual experiencing two or more depressive symptoms, which condition is not characterized according to DSM-IV as a Major Depressive Episode. For ease of reference, each of the embodiments noted above shall be understood to be encompassed within the term "depression-related mood disorders". The examples provided here are not all-encompassing, and the skilled clinician will readily recognize other conditions that can be beneficially treated by the use of $K_{ATP}$ channel openers. The term "treatment" will also be understood to include not only a complete remission of all symptoms experienced by the treated individual, but also the alleviation of one or more existing depressive symptoms, as well as the prevention of occurrence of depressive symptoms by preemptive administration of the channel opener to an individual prone to or likely to develop depressive symptoms, such as those with chronic or recurrent depression. The method of the present invention can be used for treatment of any mammal exhibiting symptoms of a depression-related mood disorder, e.g., for treatment of mammals, such as cats, dogs, rats, rabbits, horses and the like; however, in a preferred embodiment, the method is used to treat humans. Preferably, the individual to be treated is one that has been diagnosed with a condition associated with a Major Depressive Episode, more preferably Major Depressive Disorder.

In the treatment of depression-related mood disorders, the active channel opener can be administered in any way which will result in effective delivery of the active ingredient, e.g., orally, nasally, transdermally, transmucosally, intravenously, intramuscularly, subcutaneously, intraperitoneally, rectally. The chosen mode of delivery, as well as the identity of the active ingredient, will govern the form that the pharmaceutical composition will take. Methodology for formulation of active ingredients is well known, and is described, for example in Remington's Pharmaceutical Sciences, 19th ed., Mack Publishing Co., Easton, Pa., 1995, and in Goodman and Gilman's The Pharmacological Basis of Therapeutics, 11th ed., Brunton et al. Eds., McGraw-Hill, 2006, the contents of each being incorporated herein by reference. In one embodiment, one or more channel openers are the sole active agent in the formulation. In an alternate embodiment, one or more channel openers can be combined with other active agents.

As one example, pharmaceutical compositions of certain of the $K_{ATP}$ channel openers useful in the practice of the invention may contain the active ingredient in free base form, or in the form of one of its pharmaceutically acceptable salts, the latter being defined as salts that are non-toxic in the amounts and concentrations at which they are administered. Typical pharmaceutically acceptable acid addition salts include, but are not limited to, chloride, fumarate, carbonate, hydrochloride, maleate, malate, phosphate, sulfamate, acetate, citrate, lactate, phosphate, tartrate, methanesulfonate, ethanesulfonate, benzenesulfonate, p-toluenesulfonate, sulfate, succinate, cyclohexylsulfamate and quinate. Useful pharmaceutically acceptable salts also include basic addition salts such as those containing aluminum, alkylamine, calcium, ammonium, lithium, magnesium, potassium, sodium, zinc, benzathine, chloroprocaine, choline, diethanolamine, ethylenediamine, meglumine, and procaine, when acidic functional groups, such as carboxylic acid or phenol, are present on the chosen channel opener.

For ease of administration, the channel opener will usually be combined with pharmaceutically acceptable carriers or excipients. These other components of the formulation will be chosen based on the mode of administration and the form of delivery. Orally administered compositions in solid form will typically be administered in the forms of tablets, capsules, powders, granules, lozenges; such dosage forms may contain, for example, in addition to the active agent, bulking agents, binding agents, and lubricating agents, as well as enteric coatings. Oral administration may also be in liquid form, such as syrups, emulsions, liquid suspensions, or elixirs, and as such, will ordinarily contain inert liquid diluents, such as water, as well as other excipients, such as emulsifying agents, buffering agents, suspending agents or sweeteners.

Parenteral administration will typically be via injection or infusion of a sterile aqueous or non-aqueous vehicle containing the active component in solution, emulsion or suspension. Aqueous vehicles will ordinarily contain sterilized water as diluent, while non-aqueous vehicles may contain glycols, such as propylene glycol, vegetable oils, such as corn or olive oil, or injectable organic esters such as ethyl oleate.

Vaginal or rectal delivery will typically be by way of an inserted pessary or suppository. In addition to the active component, such dosage forms will ordinarily contain additional components such as glycerin, wax, gelatin as well as surfactants or other absorption promoters. All dosage forms may also contain one or more preservatives. It may also be desirable to incorporate components that provide or prolonged or extended release of the active ingredient.

The foregoing components are provided by way of example only, and the skilled artisan can readily formulate a dosage form appropriate to the chosen method of administration. The preferred mode of administration of the channel openers is oral administration.

The chosen dosage form will contain a therapeutically effective amount of at least one selected channel opener. By "therapeutically effective amount" is meant that amount of the active ingredient that will achieve the desired biological result. In the present case, in one embodiment, the desired result is stimulation of glutamate uptake system of astrocytes. "Stimulation" will be understood to mean an enhancement of the amount of glutamate uptake in the presence of the $K_{ATP}$ channel opener, over the baseline level of uptake achieved in the absence of the channel opener. In another embodiment, the desired biological result is the alleviation of at least one depressive symptom, preferably alleviation of more than one symptom, and most preferably alleviation of all depressive symptoms exhibited by the individual. In yet another embodiment, the desired result is the prevention of onset of depressive symptoms in an individual prone to or likely to develop such symptoms. In absolute terms, the therapeutically effective amount administered to an individual in need of treatment will vary depending upon a number of factors, including, but not limited to, the identity and potency of the channel opener, the species being treated, the patient's weight, severity of condition, and the chosen mode of administration. In general, the range of a single dosage will typically be between about 0.001 and about 100 mg/kg body weight. In one embodiment, particularly for human subjects using oral delivery, a single dosage is between about 0.01 and 50 mg/kg, in another embodiment between about 1 and about 10 mg/kg, in yet another embodiment, between about 2 and about 5 mg/kg. The dosage will typically be administered at least once per day, up to three times daily, for as long as the individual continues to be in need of treatment. These dosages are exemplary, however, and the skilled clinician will readily recognize modifications that may be made to suit the individual patient's needs.

The invention will be further elucidated by the following non-limiting examples:

Example I

This example illustrates the correlation between reduced glutamate uptake and learned helplessness in rats.

Brain slices from cortical tissue were removed from rats from a line showing a tendency toward helplessness (LH line) and rats from a line showing a tendency toward not becoming helpless (nLH line). N=5 in each line. The slices were placed on filters and exposed to a buffer with radioactive glutamate (GLU) or gamma amino butyric acid (GABA) at two temperatures, 0° C. and 37° C. The buffer solutions are pulled through the filters, and the counts for each filter are measured. The 0° counts represent non-specific binding and the 37° counts represent non-specific binding plus active transport, the difference between the two representing the amount of active transport. The data obtained is as follows:

| Glutamate | | |
|---|---|---|
| nLH: | GLU | 580,855 cpm/mg |
| LH: | GLU | 548,583 cpm/mg |

This shows nLH has 6% more uptake or transport than the LH line suggesting that less glutamate uptake tends to be associated with helplessness.

| GABA: | | |
|---|---|---|
| nLH: | GABA | 28,520 cpm/mg |
| LH: | GABA | 30,621 cpm/mg |

This shows nLH has 7% less GABA uptake and suggests a higher inhibitory tone is associated with helplessness.

Example II

This example illustrates the connection between reduced glutamate transporter expression and learned helplessness in rats.

Animals:

Male rats were housed in standard rodent cages on a 12-hour light-dark cycle with lights on at 7 AM. Animals were provided with food and water ad libitum.

Learned Helplessness: Breeding

Helpless lines were bred in house from Harlan Sprague-Dawley (SD) outbred rats by selective mating of animals susceptible to learned helplessness and, as a control, animals not developing learned helplessness after uncontrollable Shock. Five breeding pairs showing the most pronounced phenotype in the test for learned helplessness are selected from each strain and randomly mated. Brother-sister matings are avoided, repeated back-crosses to the paternal SD-strain ensures diversity of the gene pool and avoids incidental co-selection of genes not related to the predisposition of learned helplessness. After more than 50 generations, a cLH (congenital learned helplessness) and a cNLH (congenital not learned helplessness) lines became available, and show expected differences in the escape test for learned helplessness: over half of the cLH animals display a spontaneously helpless phenotype with 10 or more escape failures, the rest show an intermediate result with 4-9 escape failures. On the other hand, a high percentage of the cNLH rats show the expected not helpless phenotype after exposure to inescapable stress, with only a small proportion having 6 or 7 escape failures.

Learned Helplessness: Testing

At the age of 9 weeks, male rats are tested for learned helplessness. Testing consists of an escape paradigm, were 0.8 mA, 60 sec foot-shocks can be interrupted with a lever press. A trial not terminated within 20 seconds is considered a failure, and 10 or more failed trials out of 15 trials are treated as "helpless" phenotype. cNLH animals are exposed to a total of 20 unpredictable, unescapable foot-shocks (0.8 mA, 60 sec) 24 hours prior to testing.

Three cohorts of animals were selected for in situ hybridization: (I) Rats from the cNLH line exhibiting not helpless behavior (n=6, 0.83 failures in 15 trials); (II) Animals with low failure rate from the cLH line (n=6, 4.5 failures); and (III) helpless littermates of the cLH line (n=6, 12.3 failures).

Rats were sacrificed five weeks after training and testing at the age of 14 weeks. Brains were shock-frozen in isopentane before being stored at −80° C. Coronal sections (20 μm) at the level of the dorsal hippocampus (distance to the bregma: −3.80 mm) corresponding to the rat brain axis of Paxinos and Watson, (The Rat Brain in Stereotaxic Coordinates, Academic. Press, 1998) were cut in a cryostat and thaw-mounted on Superfrost Plus microscopic slides, fixed in 4% paraformaldehyde, dehydrated in ethanol, and stored at −20° C.

In situ hybridization was performed on two sections from each animal (n=6 per cohort) with $^{35}$S-UTP-labeled cRNA probes of EAAT1 (GenBank-accession number: S59158, bases 2834-3229); EAAT2 (X67857, bases 1190-1626), EAAT3 (D63772, bases 2092-2692), EAAT4 (U89608, bases 1417-1821), and vGluT1 (U07609, bases 296-720). Sub-cloned cDNAs were in vitro transcribed using T3 or T7-RNA polymerase. Efficiency of $^{35}$S-UTP incorporation was determined and hybridizations with anti-sense and sense-probes at concentration of $10^7$ cpm/ml were carried out at high stringency conditions (50% formamide, 55° C.) for 16 hrs. After several washing steps including RNAse A-digestion, slices were dehydrated and exposed to X-ray films (Biomax MR1 18×24 cm).

Quantitation of Autoradiographic Films

X-ray films were analyzed with a Sony video camera XC ST70, and the AIS Software (Applied Information Systems, Chapel Hill, USA) at the levels of the hippocampal regions dentate gyrus (DG), cornum ammonis subregions (CA1 and CA3), occipital cortex (OC), and retrosplenial granular cortex (RSG) corresponding to the retrosplenial cingulate cortex. Representative examples of vGluT1- and EAAT2-expression are depicted in FIG. 1, including demarcation of the above-mentioned regions of interest. Gray value images of the co-exposed $^{14}$C-plastic standards (Amersham Perkin Elmer, Wellesley, USA) were used to compute a calibration curve by non-linear, least squares fitting, which defined the relationship between gray values and concentration of radioactivity. Non-specific signals were assessed separately for each section in the white matter separating hippocampal CA1 and cerebral cortex. These readings were subtracted from gray values in the regions of interest (total binding) resulting in a semiquantitative determination of mRNA abundance.

Data Analysis

Data analysis was performed using the software SPSS version 14 (statistical package for social studies). Means were calculated form the individual semiquantitative assessment of gene expression levels in the regions of interest. For statistical evaluation, two-way analysis of variance for testing the hypothesis on cohort-difference (ANOVA, factor cohort). Within the analysis of variance, the post-hoc correction LSD was applied. Levels of statistical significance are depicted with asterisks: $p<: 0.05^*$; $p<0.001^{**}$; and trends ($p<0.1$) as "T". Parametric correlation coefficients were calculated between number of failures in the testing for helplessness and ISH-signal intensity including a two-tailed testing for statistical significance.

Results

The results shown in FIG. 1 demonstrate that the glutamate transporter GLT1 is expressed at significantly higher levels in not helpless rats, in comparison with expression in helpless rats, in all areas of the habenula tested, indicating a correlation between reduced glutamate uptake and the helpless condition.

Example III

This example illustrates the efficacy of a $K_{ATP}$ channel opener in alleviating the symptoms of learned helplessness in rats.

Figure 2:
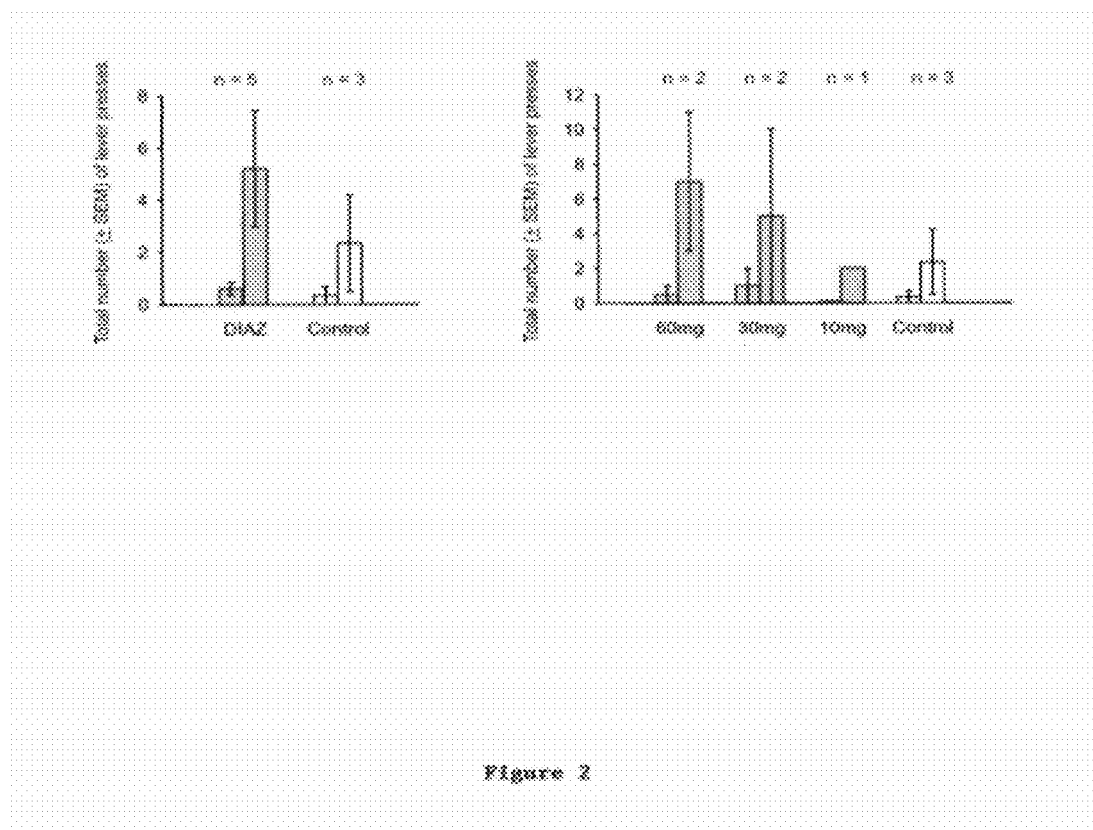
FIG. 2 illustrates the results of oral administration of diazoxide, a $K_{ATP}$ channel opener, to rats exhibiting learned helplessness, and tested as described in Example I. Successful treatment is evidenced in an increase in the number of lever presses post-treatment relative to the number of lever presses pre-treatment. The left graph illustrates the average number of lever presses based on the sum of all treated animals compared with control animals; the right graph illustrates the number of lever presses in terms of dose response in treated animals, compared with control animals.

Five rats from the cLH rat line described in Example I are provided with orally administered diazoxide dissolved in NaOH over a period of three days. Two animals received 60 mg per day two received 30 mg, and one received 10 mg. Three rats in the control group received no treatment. Each cohort was subjected to the learned helplessness testing procedure pre-treatment and post-treatment as described in Example I to determine whether the diazoxide was able to alleviate the symptoms of learned helplessness. As illustrated in FIG. 2, after only three days treatment, those rats in the treatment cohorts exhibit a substantial increase in the number of lever presses observed, indicating successful treatment of learned helplessness.

The invention claimed is:

1. A method of treating a depressive symptom in a mammal comprising administering to the mammal in need of such treatment a therapeutically effective amount of a β-lactam antibiotic in combination with a $K_{ATP}$ channel opener wherein the channel opener is selected from the group consisting of diazoxide and iptakalim.

2. A method of treating a depression-related mood disorder in a mammal comprising administering to the mammal in need of such treatment a therapeutically effective amount of a β-lactam antibiotic in combination with a $K_{ATP}$ channel opener wherein the channel opener is selected from the group consisting of diazoxide and iptakalim.

* * * * *